(12) United States Patent
Bachmann et al.

(10) Patent No.: US 11,344,489 B2
(45) Date of Patent: May 31, 2022

(54) AZOMETHINE DYE CHROMOPHORES

(71) Applicant: BASF SE, Ludwigshafen (DE)

(72) Inventors: Frank Bachmann, Basel (CH); Beate Froehling, Ludwigshafen (DE); Christian Cremer, Grenzach-Wyhlen (DE); Marie-Pascale Perritaz, Basel (CH); Volker Wendel, Düsseldorf-Holthausen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 17/294,715

(22) PCT Filed: Nov. 21, 2019

(86) PCT No.: PCT/EP2019/082009
§ 371 (c)(1),
(2) Date: May 18, 2021

(87) PCT Pub. No.: WO2020/104564
PCT Pub. Date: May 28, 2020

(65) Prior Publication Data
US 2022/0016007 A1 Jan. 20, 2022

(30) Foreign Application Priority Data
Nov. 21, 2018 (EP) ..................... 18207425

(51) Int. Cl.
*A61Q 5/10* (2006.01)
*A61K 8/49* (2006.01)
*A61K 8/365* (2006.01)
*A61K 8/41* (2006.01)
*A61Q 5/06* (2006.01)

(52) U.S. Cl.
CPC .............. *A61K 8/494* (2013.01); *A61K 8/365* (2013.01); *A61K 8/41* (2013.01); *A61Q 5/065* (2013.01); *A61K 2800/4324* (2013.01)

(58) Field of Classification Search
CPC .......... A61Q 5/10; A61Q 5/065; A61K 8/411; A61K 8/415; A61K 8/4926; A61K 8/494; A61K 8/41; A61K 8/342; A61K 8/347; A61K 8/365; A61K 2800/432; A61K 31/437; C09B 55/00
USPC .......................................................... 8/426
See application file for complete search history.

(56) References Cited

U.S. PATENT DOCUMENTS

| | | | |
|---|---|---|---|
| 4,184,844 A | 1/1980 | Grollier et al. | |
| 4,675,130 A | 6/1987 | Kalopissis et al. | |
| 9,226,883 B2* | 1/2016 | Sabelle | A61K 8/35 |
| 2015/0000688 A1 | 1/2015 | Sabelle et al. | |

FOREIGN PATENT DOCUMENTS

| | | | |
|---|---|---|---|
| FR | 2968947 A1 | 6/2012 | |
| GB | 1267635 A | 3/1972 | |
| GB | 2141437 A | 12/1984 | |
| WO | WO 2009/077390 A2 * | 6/2009 | ............... A61Q 5/10 |
| WO | WO-2015/097310 A1 | 7/2015 | |

OTHER PUBLICATIONS

STIC Search Report dated Nov. 24, 2021.*

(Continued)

*Primary Examiner* — Eisa B Elhilo
(74) *Attorney, Agent, or Firm* — Marshall, Gerstein & Borun LLP

(57) ABSTRACT

A composition for dyeing keratin fibres comprising a. at least one azomethine compound selected from compounds (3) and (4) and b. water. The composition may be used in a process for dyeing keratin fibres or, with simultaneous or sequential application of a composition comprising one or more oxidising agents, in a process for lightening keratin fibres.

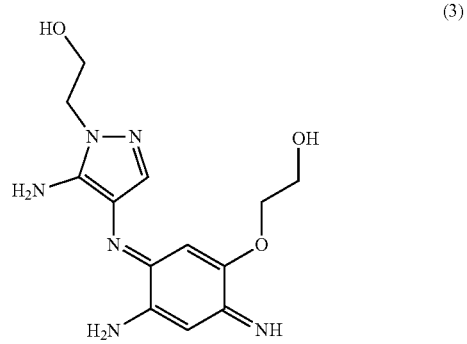

(3)

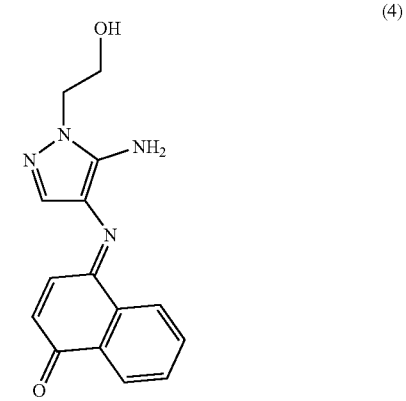

(4)

10 Claims, No Drawings

(56) References Cited

OTHER PUBLICATIONS

Brown et al., The role of meta difunctional benzene derivatives in oxidative hair dyeing. II. Reactions with p-aminophenols, J. Soc. Cosmetic Chemists, 30(4):191-211 (1979).
European Search Report for EP Patent Application No. 18207425.2, dated Feb. 20, 2019, 6 pages.
International Application No. PCT/EP2019/082009, International Search Report and Written Opinion, dated Jan. 9, 2020.
Samain, et al., "Lightening hair dyeing process using a substrate bearing an oxidizing agent and an aqueous composition comprising one or more direct dyes", DATABASE CAPLUS [Online], Chemical Abstracts Service, retrieved from STN Database accession No. 2015:1090525, XP002788242, 2015, 2 pages.
Sousa et al., Eco-friendly synthesis of indo dyes mediated by a bacterial laccase, Green Chemistry, 18(22):6063-70 (2016).
Zhang et al., A new class of oxazolidinone- and phthalimide-based oxidation dye couplers and their effect on azomethine dye color, Dyes and Pigments, 149:167-76 (2018).

* cited by examiner

AZOMETHINE DYE CHROMOPHORES

CROSS-REFERENCE TO RELATED APPLICATIONS

This is the U.S. national phase of International Application No. PCT/EP2019/082009, filed Nov. 21, 2019, which claims the benefit of European Patent Application No. 18207425.2, filed on Nov. 21, 2018.

The presently claimed invention relates to the field of dyeing keratin fibers and in particular human keratin fibers such as the hair.

The presently claimed invention relates to a composition for dyeing keratin fibers. The presently claimed invention also relates to a process for dyeing keratin fibers using the dye composition.

BACKGROUND OF THE INVENTION

It is a known practice to dye keratin fibers, and in particular the hair, with dye compositions containing one or more direct dyes, according to a "direct dyeing" process. The process involves applying a composition comprising one or more direct dyes to the keratin fibers, allowing the composition to contact with the fibers for a requisite time, and then rinsing the fibers. The direct dyes used hitherto are generally nitrobenzene dyes, anthraquinone dyes, nitropyridine dyes, dyes of azo, xanthene, acridine or azine type or triarylmethane-based dyes.

However, the use of these direct dyes is associated with drawbacks. The colorations resulting therefrom are temporary or semi-permanent. The nature of the interactions that bind these direct dyes to the keratin fiber and their desorption from the surface and/or the core of the fiber are responsible for their weak dyeing power. Further, the above mentioned direct dyes provide poor fastness with respect to washing, inclement weather or perspiration.

Moreover, such direct dyes are generally sensitive to the action of oxidizing agents such as aqueous hydrogen peroxide solution, which makes them difficult to use in lightening direct dye compositions that are formulated with aqueous hydrogen peroxide solution and a basifying agent, these compositions resembling the compositions used for oxidation dyeing. In other words, direct dyes are generally sparingly compatible with dye compositions intended for lightening fibers, and, consequently, their use in a lightening dyeing process, as an alternative to oxidation dyeing, is unsatisfactory.

These direct dyes are also associated with the drawback of lacking light-fastness because of the poor resistance of the chromophore to photochemical attack. This lack of stability leads to fading over time of the coloration of the keratin fibers.

US 2015/000688 A1 discloses direct dyes of azomethine type and their use for dyeing keratin fibers.

FR 2968947 A1 discloses a dye composition comprising benzyl alcohol, at least one $C_1$-$C_4$ monoalcohol and at least one direct dye of azomethine type for dyeing keratin fibers.

GB 2141437 A discloses direct dyes based on indoaniline and indophenol compounds and compositions thereof for hair dyeing.

There is thus a need for compositions containing direct dyes that dye keratin fibers satisfactorily and that are light-fast. Further, it is desired that these compositions are capable of providing colorations that are both resistant to the various attacking factors to which the fibers may be subjected, such as inclement weather, sunlight, washing and perspiration, and that are also sufficiently stable in the presence of oxidizing agents such as aqueous hydrogen peroxide solution in order to be able to obtain simultaneous lightening of the fibers with the advantages outlined above.

Hence, it is an object of the presently claimed invention to provide compositions containing direct dyes that dye keratin fibers satisfactorily, that are light-fast, that are capable of providing colorations that are both resistant to the various attacking factors to which the fibers may be subjected, such as inclement weather, sunlight, washing and perspiration, and that are also sufficiently stable in the presence of oxidizing agents such as aqueous hydrogen peroxide solution.

SUMMARY OF THE INVENTION

It was surprisingly found that the above identified object is met by the subject matter of the claims.

In the following, specific embodiments of the present invention are described:

1. A composition for dyeing keratin fibers comprising
   a. at least one azomethine compound of the formula (1);

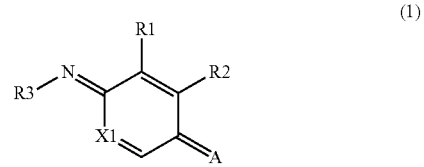

wherein, $R_1$ is hydrogen, or $C_1$-$C_5$ alkyl;

$R_2$ is hydrogen, $C_1$-$C_5$ alkyl, a radical of formula *—O—$(CH_2)_n$—OH; or $R_1$ and $R_2$ together form a radical of formula

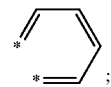

A is NH, or O;

$X_1$ is

or *—N=*;

$R_3$ is a radical of formula

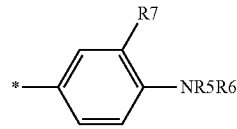 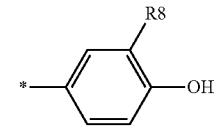

-continued

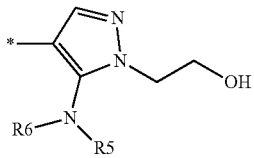 or 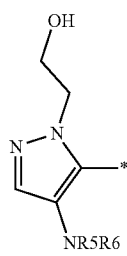

$R_4$ is hydrogen, or $NH_2$;
$R_5$, $R_6$, $R_7$ and $R_8$, independently from each other are hydrogen, or $C_1$-$C_5$ alkyl; and
n is a number from 1 to 3;
and
b. water.

2. The composition according to embodiment 1, wherein
$R_1$ is hydrogen; or $R_1$ and $R_2$ together form a radical of formula

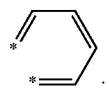.

3. The composition according to any of embodiments 1 to 2, wherein
$R_3$ is a radical of formula

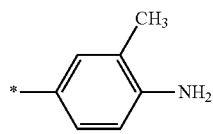 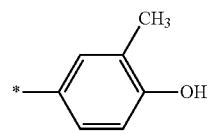

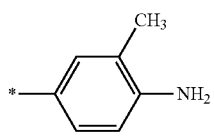 or 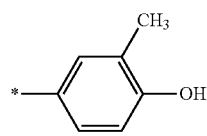

4. The composition according to any of embodiments 1 to 3, wherein
$R_1$ is hydrogen; or $R_1$ and $R_2$ form a radical of formula;

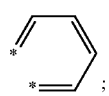

$R_2$ is hydrogen, methyl or a radical of formula *—O—$(CH_2)_2$—OH;
A is =NH, or O—;
$X_1$ is

or* —CH=; and
$R_3$ is a radical of formula

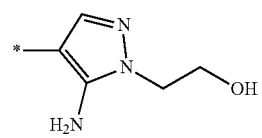

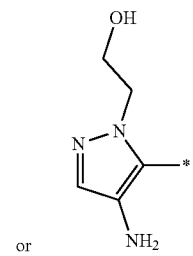

5. The composition according to any of embodiments 1 to 4, wherein compound of the formula (1) is selected from

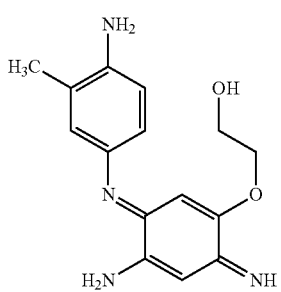 (2)

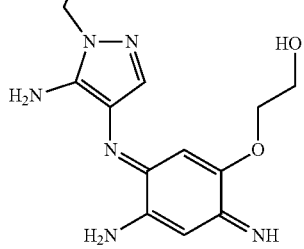 (3)

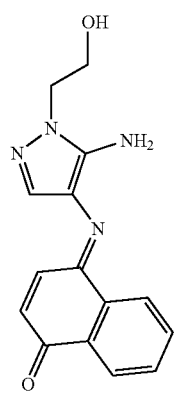

(4)

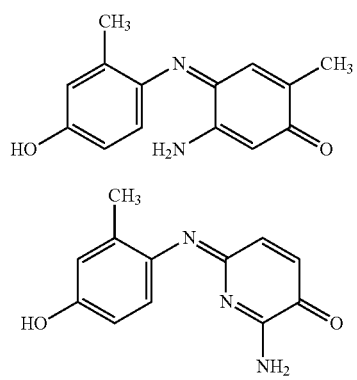

(5)

(6)

6. The composition according to any of embodiments 1 to 5, wherein the amount of azomethine compound is in the range from 0.001% to 10% by weight based on the total weight of composition.
7. The composition according to any of embodiments 1 to 6 having a pH in the range from 3 to 12.
8. The composition according to any of embodiments 1 to 7 further comprising a nonionic surfactant.
9. The composition according to any of embodiments 1 to 8 further comprising an organic solvent selected from the group consisting of $C_1$-$C_4$ alkanols, polyols, polyol ethers, and aromatic alcohols.
10. The composition according to any of embodiments 1 to 9 further comprising at least one oxidation dye in an amount in the range of 0.001% to 10% by weight based on the total weight of composition, and at least one coupler in an amount in the range of 0.001% to 10% by weight based on the total weight of composition.
11. The composition according to any of embodiments 1 to 10 further comprising an adjuvant in amount in the range of 0.01% to 20% by weight based on the total weight of composition, wherein the adjuvant is at least one selected from the group consisting of surfactants, polymers, thickeners, antioxidants, penetrants, solubilizers, sequestrants, fragrances, buffers, dispersants, conditioning agents, film-forming agents, ceramides, preserving agents, opacifiers, conductive polymers and combinations thereof.
12. A use of the composition according to any of embodiments 1 to 11 for dyeing keratin fibers.
13. The use of the composition according to embodiment 12 for dyeing human hair.
14. A process for dyeing keratin fibers, characterized in that the composition according to any of embodiments 1 to 11 is applied to the wet or dry fibers for a time that is sufficient to obtain the desired coloration, after which the fibers are rinsed, optionally washed with shampoo and rinsed again, and the resulting fibers are dried or left to dry to obtain dyed keratin fibers.
15. A process for lightening keratin fibers, characterized in that
   (i) the dye composition according to any of embodiments 1 to 11, free of oxidizing agent, and
   (ii) a cosmetic composition comprising one or more oxidizing agents are applied to the fibers; compositions (i) and (ii) being applied to the keratin fibers sequentially or simultaneously for a time that is sufficient to obtain the desired lightening, and the fibers are then rinsed, optionally washed with shampoo and rinsed again, and the resulting fibers are dried or left to dry.

DETAILED DESCRIPTION OF THE INVENTION

Before the present process of the invention and various embodiments are described in detail, it is to be understood that this invention is not limited to particular process described, since such processes may, of course, vary. It is also to be understood that the terminology used herein is not intended to be limiting, since the scope of the present invention will be limited only by the appended claims.

If hereinafter a group is defined to comprise at least a certain number of embodiments, this is meant to also encompass a group which preferably consists of these embodiments only. In case the terms "first", "second", "third" or "i)", "ii)", "iii)", or "(A)", "(B)" and "(C)" or "(a)", "(b)", "(c)", "(d)", etc. relate to steps of a method or use or assay there is no time or time interval coherence between the steps, that is, the steps may be carried out simultaneously or there may be time intervals of seconds, minutes, hours, days, weeks or even months between such steps, unless otherwise indicated in the application as set forth herein above or below.

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

Hence, in an aspect, the presently claimed invention provides a composition for dyeing keratin fibers. The composition comprises a) at least one azomethine compound of the formula (1);

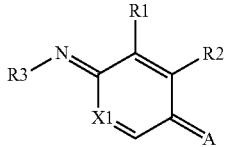
(1)

wherein, $R_1$ is hydrogen, or $C_1$-$C_5$ alkyl;

$R_2$ is hydrogen, $C_1$-$C_5$ alkyl, a radical of formula *—O—$(CH_2)_n$—OH; or $R_1$ and $R_2$ together form a radical of formula

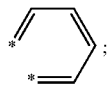;

A is NH, or O;

$X_1$ is

, or *—N=*;

$R_3$ is a radical of formula

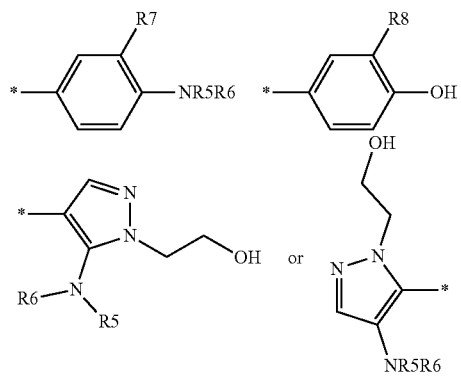

$R_4$ is hydrogen, or $NH_2$;

$R_5$, $R_6$, $R_7$ and $R_8$ independently from each other are hydrogen, or $C_1$-$C_5$ alkyl; and n is a number from 1 to 3;

and b) water.

The term "alkyl", as used herein, refers to an acyclic saturated aliphatic group that is solely constituted of carbon atoms and hydrogen atoms, including linear or branched alkyl residues. Furthermore, the alkyl residue is preferably unsubstituted.

Preferably, $R_1$ is hydrogen; or $R_1$ and $R_2$ together form a radical of formula

.

Preferably, $R_3$ is a radical of formula

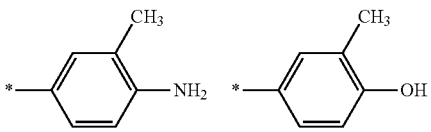

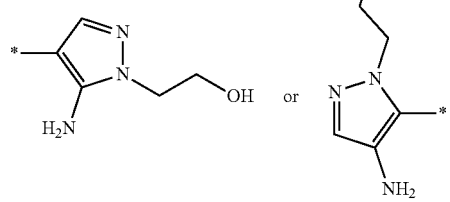

Preferably, $R_1$ is hydrogen; or $R_1$ and $R_2$ form a radical of formula

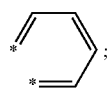;

$R_2$ is hydrogen, methyl or a radical of formula *—O—$(CH_2)_2$—OH;

A is =NH, or O—;

$X_1$ is

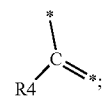;

or* —CH=; and $R_3$ is a radical of formula

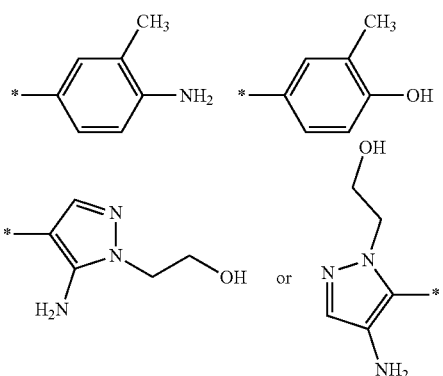

More preferably, the azomethine compound of formula (1) is selected from compounds of formula (2) to (6).

(2)
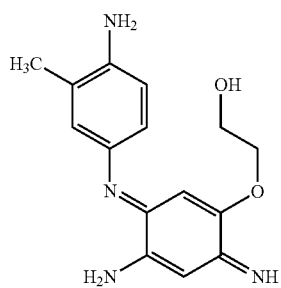

(3)
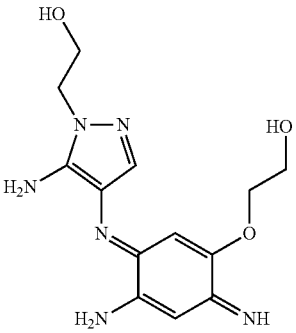

(4)
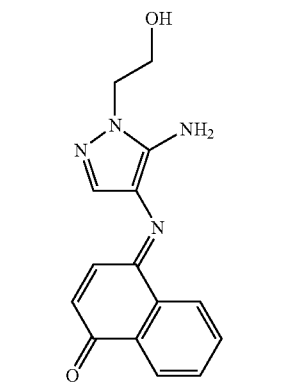

(5)
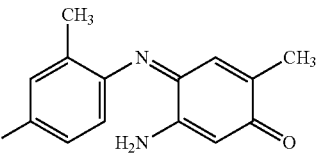

(6)
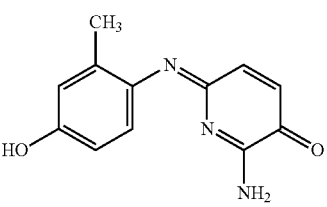

The azomethine compounds of formula (1) act as direct dyes. Compositions according to the presently claimed invention dye keratin fibers, and produce powerful, chromatic and sparingly selective colorations on the keratin fibers.

The azomethine compounds of formula (1) can be prepared by the reaction of an oxidation base with a coupler in the presence of an oxidizing agent by known procedures, for example the procedure described in J. F. Corbett, J. Chem. Soc. B, (1969), 207 and J. F. Corbett, J. Chem. Soc. Perkin II (107?), 53. Preferably, the oxidizing agent is hydrogen peroxide.

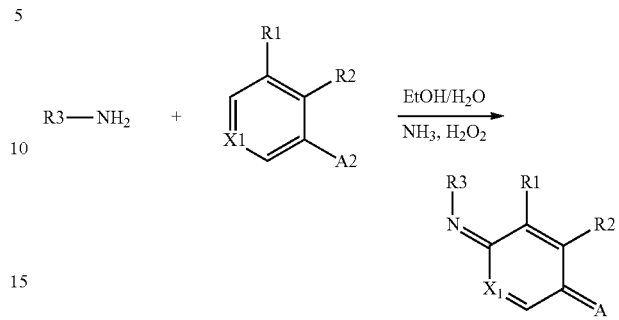

wherein,
$R_1$ is hydrogen, or $C_1$-$C_5$ alkyl;
$R_2$ is hydrogen, $C_1$-$C_5$ alkyl, a radical of formula *—O—$(CH_2)_n$—OH; or
$R_1$ and $R_2$ together form a radical of formula

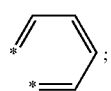;

$A_2$ is $NH_2$, or OH;
$X_1$ is

, or *—N=*;
$R_3$ is a radical of formula

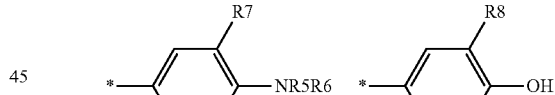

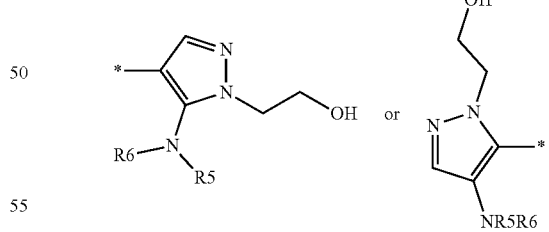

$R_4$ is hydrogen, or $NH_2$;
$R_5$, $R_6$, $R_7$ and $R_8$ independently from each other are hydrogen, or $C_1$-$C_5$ alkyl; and
n is a number from 1 to 3.

Furthermore, these compositions provide dyed keratin fibers having colorations that are very resistant to the various attacking factors to which keratin fibers may be exposed, such as inclement weather, light, washing and perspiration. Thus, the composition of the presently claimed invention displays good colour fastness.

Preferably, the amount of the azomethine compound of the formula (1) in the composition is in the range from 0.001% to 10% by weight based on the total weight of composition.

More preferably, the amount of the azomethine compound of the formula (1) in the composition is in the range from 0.005% to 6% by weight based on the total weight of composition.

Preferably, the composition of the presently claimed invention has a pH in the range from 3 to 12.

More preferably, the composition of the presently claimed invention has a pH in the range from 5 to 11.

Preferably, the composition of the presently claimed invention further comprises a non-ionic surfactant. Non-ionic surfactants contain a hydrophilic group, such as, a polyol group, a polyalkylene glycol ether group or a combination of polyol and polyglycol ether groups. The non-ionic surfactants are selected from the group consisting of:
- addition products of 2 to 30 mol of ethylene oxide and/or 0 to 5 mol of propylene oxide with linear fatty alcohols having 8 to 22 carbon atoms, with fatty acids having 12 to 22 carbon atoms and with alkylphenols having 8 to 15 carbon atoms in the alkyl group,
- $C_{12}$-$C_{22}$ fatty acid mono- and di-esters of addition products of 1 to 30 mol of ethylene oxide with glycerol,
- $C_8$-$C_{22}$ alkyl-mono- and -oligo-glycosides and ethoxylated analogues thereof,
- addition products of 5 to 60 mol of ethylene oxide with castor oil and hydrogenated castor oil,
- addition products of ethylene oxide with sorbitan fatty acid esters,
- addition products of ethylene oxide with fatty acid alkanolamides.

More preferably, the non-ionic surfactant is decyl glucoside.

Water is the medium of the dyeing composition of the presently claimed invention. However, an organic solvent may be required to aid solubility of the components in order to obtain a homogeneous mixture.

Preferably, the composition of the presently claimed invention further comprises an organic solvent selected from the group consisting of $C_1$-$C_4$ alkanols, polyols, polyol ethers, and aromatic alcohols.

The composition of the presently claimed invention further preferably comprises at least one oxidation dye in an amount in the range of 0.001% to 10% by weight based on the total weight of the composition, and preferably at least one coupler in an amount in the range of 0.001% to 10% by weight based on the total weight of composition.

Preferably, the composition comprises the at least one oxidation dye in an amount in the range from 0.005% to 6% by weight relative to the total weight of the composition. Preferably, the composition comprises the at least one coupler in an amount in the range from 0.005% to 6% by weight relative to the total weight of the composition.

Preferably, the composition of the presently claimed invention further comprises an adjuvant in amount in the range of 0.01% to 20% by weight based on the total weight of composition.

Preferably, the adjuvant is at least one selected from the group consisting of surfactants, polymers, thickeners, antioxidants, penetrants, solubilizers, sequestrants, fragrances, buffers, dispersants, conditioning agents, film-forming agents, ceramides, preserving agents, opacifiers, conductive polymers and combinations thereof.

Further, a person skilled in the art will take care to select this or these optional additional compound(s) such that the advantageous properties intrinsically associated with the dye composition in accordance with the invention are not, or are not substantially, adversely affected by the envisaged addition(s).

In another aspect, the presently claimed invention provides a use of the composition for dyeing keratin fibers.

In accordance with the preferred embodiments of the presently claimed invention, the composition is used for dyeing human hair.

Compositions according to the invention are light-fast and they can be used in the presence of an oxidizing agent, which facilitates their use in lightening direct dyeing compositions based on oxidizing agents. In other words, the compositions according to the presently claimed invention lead to fast colorations that are compatible with dye compositions intended for lightening keratin fibers.

Azomethine Compound

The azomethine compound of the formula (1) is formed by the reaction of oxidation base with a coupler in the presence of an oxidizing agent. Preferably, the oxidation agent is hydrogen peroxide.

The oxidation base is preferably selected from the group consisting of paraphenylenediamines, bis(phenyl)alkylenediamines, para-aminophenols, ortho-aminophenols, heterocyclic bases, and addition salts thereof.

The para-phenylenediamine oxidation base is preferably selected from the group consisting of para-phenylenediamine, para-tolylenediamine, 2-chloro-para-phenylenediamine, 2,3-dimethyl-paraphenylenediamine, 2,6-dimethyl-para-phenylenediamine, 2,6-diethyl-paraphenylenediamine, 2,5-dimethyl-paraphenylenediamine, N,N-dimethyl-para-phenylenediamine, N,N-diethyl-para-phenylenediamine, N,N-dipropylparaphenylenediamine, 4-amino-N,N-diethyl-3-methylaniline, N,N-bis(p-hydroxyethyl)para-phenylenediamine, 4-N,N-bis(p-hydroxyethyl)-amino-2-methylaniline, 4-N,N-bis(p-hydroxyethyl)-amino-2-chloroaniline, 2-p-hydroxyethyl-paraphenylenediamine, 2-fluoro-p-phenylenediamine, 2-isopropyl-p-phenylenediamine, N-(p-hydroxypropyl)-p-phenylenediamine, 2-hydroxymethyl-p-phenylenediamine, N,N-dimethyl-3-methyl-p-phenylenediamine, N-ethyl-N-(p-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-p-hydroxyethyloxy-para-phenylenediamine, 2-pacetylaminoethyloxy-para-phenylenediamine, N-(p-methoxyethyl)-para-phenylenediamine, 4-aminophenylpyrrolidine, 2-thienyl-paraphenylenediamine, 2-p-hydroxyethylamino-5-aminotoluene and 3-hydroxy-1-(4'-aminophenyl) pyrrolidine, and addition salts thereof with an acid.

More preferably, the para-phenylenediamine oxidation base is selected from the group consisting of para-phenylenediamine, para-tolylenediamine, 2-isopropyl-paraphenylenediamine, 2-(p-hydroxyethyl)-para-phenylenediamine, 2-(p-hydroxyethyloxy)-paraphenylenediamine, 2,6-dimethyl-para-phenylenediamine, 2,6-diethyl-paraphenylenediamine, 2,3-dimethyl-para-phenylenediamine, N,N-bis(p-hydroxyethyl)paraphenylenediamine, 2-chloro-para-phenylenediamine, 2-(p-acetylaminoethyloxy)-paraphenylenediamine and their addition salts with an acid.

The bis(phenyl)alkylenediamine oxidation base is preferably selected from the group consisting of N,N'-bis(p-hydroxyethyl)-N,N'-bis(4'-aminophenyl)-1,3-diaminopropanol, N,N'-bis(p-hydroxyethyl)-N,N'-bis(4'-aminophenyl) ethylenediamine, N,N'-bis(4-aminophenyl) tetramethylenediamine, N,N'-bis(p-hydroxyethyl)-N,N'-bis (4-aminophenyl) tetramethylenediamine, N,N'-bis(4- methylaminophenyl)tetramethylenediamine, N,N'-bis (ethyl)-N,N'-bis(4'-amino-3'-methylphenyl)ethylenediamine and 1,8-bis(2, 5-diaminophenoxy)-3,6-dioxaoctane, and their addition salts with an acid.

The para-aminophenol oxidation base is preferably selected from the group consisting of para-aminophenol, 4-amino-3-methylphenol, 4-amino-3-fluorophenol, 4-amino-3-chlorophenol, 4-amino-3-hydroxymethyl)phenol, 4-amino-2-methylphenol, 4-amino-2-(hydroxymethyl)phenol, 4-amino-2-(methoxymethyl)phenol, 4-amino-2-(aminomethyl)phenol, 4-amino-2-[(p-hydroxyethyl)aminomethyl]phenol, 4-amino-2-fluorophenol and their addition salts with an acid.

The ortho-aminophenol oxidation base is preferably selected from the group consisting of 2-aminophenol, 2-amino-5-methylphenol, 2-amino-6-methylphenol, 5-acetamido-2-aminophenol and their addition salts with an acid.

The heterocyclic oxidation base is preferably selected from the group consisting of pyridine derivatives, pyrimidine derivatives and pyrazole derivatives. The pyridine derivative is preferably selected from the group consisting of the compounds described, for example, in patents GB 1 026 978 and GB1153196, such as 2, 5-diaminopyridine, 2-(4-methoxyphenyl)amino-3-aminopyridine, 3,4-diaminopyridine and their addition salts. Other pyridine oxidation base that are used in the composition of the presently claimed invention are 3-aminopyrazolo[1,5-a]pyridine oxidation bases or their addition salts described, for example, in FR 2 801 308. The pyrazole derivative is preferably selected from the group consisting of pyrazolo[1,5-a]pyrid-3-ylamine, 2-(acetylamino)pyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1, 5-a]pyrid-7-yl)ethanol, (3-aminopyrazolo[1,5-a]pyrid-2-yl)methanol, 3,6-diaminopyrazolo[1, 5-a]pyridine, 3,4-diaminopyrazolo[1,5-a]pyridine, pyrazolo[1, 5-a]pyridine-3, 7-diamine, 7-(morpholin-4-yl)pyrazolo[1, 5-a]pyrid-3-ylamine, pyrazolo[1,5-a]pyridine-3, 5-diamine, 5-(morpholin-4-yl)pyrazolo[1,5-a]pyrid-3-ylamine, 2-[(3-amino pyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1, 5-a]pyridin-5-ol, 3-aminopyrazolo[1,5-a]pyridin-4-ol, 3-aminopyrazolo[1, 5-a]pyridin-6-ol, 3-aminopyrazolo[1, 5-a]pyridin-7-ol and their addition salts.

The pyrimidine derivative is preferably selected from the group consisting of the compounds described, for example, in patents DE 2359399, JP 88-169571, JP 05-63124 and EP 0 770 375 or patent application WO96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

The pyrazole derivative is preferably selected from the group consisting of the compounds described in the patents DE 3843892, DE 4133957 and patent applications WO 94/08969, WO 94/08970, FR-A-2 733749 and DE 195 43 988, such as 4,5-diamino-1-methylpyrazole, 4,5-diamino-1-(p-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(p-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(p-hydroxyethyl)amino-1-methylpyrazole, 4,5-diamino-1-(p-methoxyethyl)pyrazole and the addition salts thereof. Further, the pyrazole derivative is selected from the group consisting of diamino-N,N-dihydropyrazolopyrazolones and those described in patent application FRA-2 886 136, such as 2,3-diamino-6, 7-dihydro-1H,5H-pyrazolo[1,2-a]pyrazol-1-one, 2 ethylamino-6,7-dihydro-1H,5H-pyrazolo[1,2-a]pyrazol-1-one, 2-amino-3-isopropylamino-6,7-dihydro-1H, 5H-pyrazolo-[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di(2-hydroxyethyl)-1,2-dihydropyrazol-3-2-amino-3-(2-hydroxyethyl)amino-6,7-dihydro-1H,5H-pyrazolo[1,2-a]pyrazol-1-one, 2-amino-3-dimethylamino-6,7-dihydro-1H, 5H-pyrazolo[1,2-a]pyrazol-1-one, 2,3-diamino-5,6,7,8-tetrahydro-1H,6H-pyridazino[1, 2-a]pyrazol-1-one, 4-amino-1,2-diethyl-5-(pyrrolidin-1-yl)-1,2-dihydropyrazol-1-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo-[1,2-a]pyrazol-1-one and the addition salts thereof.

More preferably, the pyrazole derivative is selected from the group consisting of 4,5-diamino-1-(p-hydroxyethyl)pyrazole, 2,3-diamino-6,7-dihydro-1H,5H-pyrazolo[1,2-a]pyrazol-1-one and/or a salt thereof.

The coupler is preferably selected from the group consisting of meta-phenylenediamines, meta-aminophenols, meta-diphenols, naphthalene-based couplers, heterocyclic couplers, and the addition salts thereof.

More preferably, the coupler is selected from the group consisting of 1,3-dihydroxybenzene, 1,3-dihydroxy-2-methylbenzene, 4-chloro-1,3-dihydroxybenzene, 2,4-diamino-1-(p-hydroxyethyloxy)benzene, 2-amino-4-(p-hydroxyethylamino)-1-methoxybenzene, 1,3-diaminobenzene, 1,3-bis(2, 4-diaminophenoxy)propane, 3-ureidoaniline, 3-ureido-1-dimethylaminobenzene, 2H-1,3-benzodioxol-5-ol (sesamol), 1-hydroxyethylamino-3,4-methylenedioxybenzene, o-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2, 6-dimethoxypyridine, 1-N-(p-hydroxyethyl)amino-3, 4-methylenedioxybenzene, 2, 6-bis(p-hydroxyethylamino) toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1, 5-b]-1,2,4-triazole, 2,6-dimethyl[3,2-c]-1,2,4-triazole and 6-methylpyrazolo[1,5-a]benzimidazole, the addition salts thereof with an acid.

The addition salts of the oxidation bases and couplers that are used in the compositions of the presently claimed invention are preferably selected from the addition salts with an acid such as the hydrochlorides, hydrobromides, sulfates, citrates, succinates, tartrates, lactates, tosylates, benzenesulfonates, phosphates and acetates.

Direct Dyes

The dye composition further preferably comprises additional direct dyes other than the direct azomethine dyes of the formula (1).

The additional direct dye(s) according to the invention are preferably selected from nitrobenzene dyes, neutral, azo direct dyes, quinone dyes and in particular anthraquinone direct dyes, azine direct dyes, triarylmethane direct dyes, azomethine direct dyes other than those of formula (1) and natural direct dyes.

Preferably, the nitrobenzene direct dye is selected from 1,4-diamino-2-nitrobenzene, 1-amino-2-nitro-4-β-hydroxyethylaminobenzene, 1-amino-2-nitro-4-bis(β-hydroxyethyl)aminobenzene, 1,4-bis(β-hydroxyethylamino)-2-nitrobenzene, 1-β-hydroxyethylamino-2-nitro-4-bis(p-hydroxyethylamino)benzene, 1-β-hydroxyethylamino-2-nitro-4-aminobenzene, 1-β-hydroxyethylamino-2-nitro-4-(ethyl)(p-hydroxyethyl)aminobenzene, 1-amino-3-methyl-4-β-hydroxyethylamino-6-nitrobenzene, 1-amino-2-nitro-4-β-hydroxyethylamino-5-chlorobenzene, 1,2-diamino-4-nitrobenzene, 1-amino-2-β-hydroxyethylamino-5-nitrobenzene, 1,2-bis(p-hydroxyethylamino)-4-nitrobenzene, 1-amino-2-tris(hydroxymethyl)methylamino-5-nitrobenzene, 1-hydroxy-2-amino-5-nitrobenzene, 1-hydroxy-2-amino-4-nitrobenzene, 1-hydroxy-3-nitro-4-aminobenzene, 1-hydroxy-2-amino-4,6-dinitrobenzene, 1-β-hydroxyethyloxy-2-β-hydroxyethylamino-5-nitrobenzene, 1-methoxy-2-β-hydroxyethylamino-5-nitrobenzene, 1-β-hydroxyethyloxy-3-methylamino-4-nitrobenzene, 1-β,γ-dihydroxypropyloxy-3-methylamino-4-nitrobenzene, 1-β-hydroxyethylamino-4-β,γ-dihydroxypropyloxy-2-nitrobenzene, 1-β,γ-dihydroxypropylamino-4-trifluoromethyl-2-nitrobenzene, 1-β-hydroxyethylamino-4-trifluoromethyl-2-nitrobenzene, 1-β-hydroxyethylamino-3-methyl-2-nitrobenzene, 1-β-aminoethylamino-5-methoxy-2-nitrobenzene, 1-hydroxy-2-chloro-6-ethylamino-4-nitrobenzene, 1-hydroxy-2-chloro-6-amino-4-nitrobenzene, 1-hydroxy-6-bis(β-hydroxyethyl)amino-3-nitrobenzene, 1-β-hydroxyethylamino-2-nitrobenzene, and 1-hydroxy-4-β-hydroxyethylamino-3-nitrobenzene.

The azo direct dye is preferably selected from the group consisting of the cationic azo dyes described in the patent applications WO 95/15144, WO-95/01772 and EP714954, the content of which forms an integral part of the invention, such as 1,3-dimethyl-2-[[4-(dimethylamino)-phenyl]-azo]-1H-imidazolium chloride, 1,3-dimethyl-2-[(4-aminophenyl)azo]-1H-imidazolium chloride, 1-methyl-4-[(methylphenylhydrazono)methyl]pyridinium methylsulfate. The azo direct dyes are also selected from the dyes described in the Colour Index International, 3$^{rd}$ edition, such as Disperse Red 17, Acid Yellow 9, Acid Black 1, Basic Red 22, Basic Red 76, Basic Red 51, Basic Yellow 57, Basic Brown 16, Acid Yellow 36, Acid Orange 7, Acid Red 33, Acid Red 35, Basic Brown 17, Acid Yellow 23, Acid Orange 24, Disperse Black 9, 1-(4'-aminodiphenylazo)-2-methyl-4-bis(β-hydroxyethyl)aminobenzene and 4-hydroxy-3-(2-methoxyphenylazo)-1-naphthalenesulfonic acid.

The quinone direct dye is preferably selected from Disperse Red 15, Solvent Violet 13, Acid Violet 43, Disperse Violet 1, Disperse Violet 4, Disperse Blue 1, Disperse Violet 8, Disperse Blue 3, Disperse Red 11, Acid Blue 62, Disperse Blue 7, Basic Blue 22, Disperse Violet 15, Basic Blue 99, and also the following compounds: 1-N-methylmorpholiniumpropylamino-4-hydroxyanthraquinone, 1-aminopropylamino-4-methylminoanthraquinone, 1-aminopropylaminoanthraquinone, 5-β-hydroxyethyl-1,4-diaminoanthraquinone, 2-aminoethylaminoanthraquinone, 1,4-bis(β,γ-dihydroxypropylamino)anthraquinone.

The azine direct dye is preferably selected from Basic Blue 17 and Basic Red 2. The phenoxazine direct dye is Basic Blue 124.

The triarylmethane direct dye is preferably selected from Basic Green 1, Acid Blue 9, Basic Violet 3, Basic Violet 14, Basic Blue 7, Acid Violet 49, Basic Blue 26, Acid Blue 7.

The azomethine direct dye other than those of formula (1) is preferably selected from 2-β-hydroxyethylamino-5-[bis (p-4'-hydroxyethyl)amino]-anilino-1,4-benzoquinone, 2-β-hydroxyethylamino-5-(2'-methoxy-4'-amino)anilino-1,4-benzoquinone, 3-N-(2'-chloro-4'-hydroxy)phenylacetylamino-6-methoxy-1,4-benzoquinoneimine, 3-N-(3'-chloro-4'-methylamino)phenylureido-6-methyl-1,4-benzoquinoneimine, and 3-[4'-N-(ethyl, carbamylmethyl)amino]phenylureido-6-methyl-1,4-benzoquinoneimine.

The natural direct dye is preferably selected from lawsone, juglone, alizarin, purpurin, carminic acid, kermesic acid, purpurogallin, protocatechaldehyde, indigo, isatin, curcumin, spinulosin and apigenidin. Extracts or decoctions containing these natural dyes and in particular poultices or henna-based extracts may also be used.

Preferably, the amount of the additional direct dye in the dye composition of presently claimed invention is in a range from 0.001% to 10% by weight based on the total weight of the dye composition.

More preferably, the amount of the additional direct dye in the dye composition of presently claimed invention is in a range from 0.005% to 6% by weight based on the total weight of the dye composition.

The desired pH of the dye composition is preferably achieved by means of acidifying or basifying agents commonly used in the dyeing of keratin fibers, or alternatively using standard buffer systems.

Acidifying Agent

The acidifying agent is preferably selected from mineral or organic acids other than dicarboxylic acids, such as hydrochloric acid, ortho-phosphoric acid, sulfuric acid, sulfonic acids, and carboxylic acids such as acetic acid, tartaric acid, citric acid or lactic acid.

Basifying Agent

The basifying agent is preferably selected from aqueous ammonia, alkali metal carbonates, alkanolamines such as mono-, di- and triethanolamines and their derivatives, sodium hydroxide or potassium hydroxide, and the compounds of formula (7);

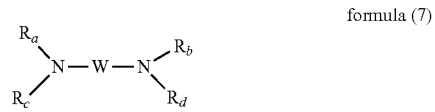

formula (7)

wherein, W is a propylene residue optionally substituted with a hydroxyl group or a $C_1$-$C_4$ alkyl radical; and $R_a$, $R_b$, $R_c$ and $R_d$ which may be identical or different, represent a hydrogen atom or a $C_1$-$C_4$ alkyl or $C_1$-$C_4$ hydroxyalkyl radical.

In accordance with the embodiments of the presently claimed invention, the composition is preferably present in the form of a liquid, a cream, a gel, or other forms which are appropriate for dyeing of keratin fibers, and in particular of human hair.

In another aspect, the presently claimed invention provides a process for dyeing keratin fibers. The process is characterized in that the composition of the presently claimed invention is applied to the wet or dry fibers for a time that is sufficient to obtain the desired coloration, after which the fibers are rinsed, optionally washed with shampoo and rinsed again. The resulting fibers are dried or left to dry to obtain dyed keratin fibers.

The presently claimed invention also provides a process for lightening keratin fibers. The process is characterized in that
  (i) the dye composition of the presently claimed invention, free of oxidizing agent, and
  (ii) a cosmetic composition comprising one or more oxidizing agents are applied to the fibers; compositions (i) and (ii) being applied to the keratin fibers, sequentially or simultaneously, for a time that is sufficient to obtain the desired lightening, and the fibers are then rinsed, optionally washed with shampoo and rinsed again. The resulting fibers are dried or left to dry to obtain light keratin fibers.

Preferably, the time required for the dye composition to achieve desired coloration or desired lightening is in the range between 1 and 60 minutes, more preferably between 5 and 40 minutes and even more preferably between 10 and 30 minutes.

The dye composition is preferably applied to the keratin fibers at a temperature range of 15-55° C. more preferably from 20-30° C.

For the purposes of the presently claimed invention, the term "sequentially" means that the oxidizing composition is applied before or after the dye composition, i.e. as a pretreatment or a posttreatment.

The oxidizing agents are preferably selected from hydrogen peroxide, urea peroxide, alkali metal bromates, persalts such as perborates and persulfates, peracids, and oxidase enzymes (with the possible cofactors thereof), such as peroxidases, 2-electron oxidoreductases for instance uricases, and 4-electron oxygenases, for instance laccases. More preferably, the oxidizing agent is hydrogen peroxide.

The oxidizing composition may contain various adjuvants conventionally used in compositions for dyeing the hair and as defined previously. The pH of the oxidizing composition containing the oxidizing agent is such that, after mixing with the dye composition, the pH of the resulting composition applied to the keratin fibers preferably ranges between 3 and 12 approximately, even more preferentially between 5 and 11 and yet more particularly between 6 and 8.5. It may be adjusted to the desired value by means of acidifying or basifying agents usually used in the dyeing of keratin fibers and as defined previously.

In accordance with an embodiment of the presently claimed invention, the dye composition according to the presently claimed invention is first prepared in a container such as a test glass before applying to keratin fibers. The preparation may be carried without oxidation agent, i.e. hydrogen peroxide and/or ammonia. The hair can be dyed with good results using the uncharged dyes.

In accordance with another embodiment of the presently claimed invention, the dye composition is present in the form of a multi-compartment device or "kit".

A multi-compartment device or "kit" preferably comprises:
  (a) a first compartment or part containing the composition of the presently claimed invention, free of oxidizing agent; and
  (b) a second compartment or part comprising one or more oxidizing agents.

Having generally described the invention, a further understanding can be obtained by reference to certain specific examples which are provided herein for the purpose of illustration only, and are not intended to be limiting unless otherwise specified.

EXAMPLES

A. Synthesis Examples

All reactions have been performed under a nitrogen atmosphere.

Example 1: 2-[4-amino-3-(4-amino-3-methyl-phenyl)imino-6-imino-cyclohexa-1,4-diene-1-yl]oxyethanol

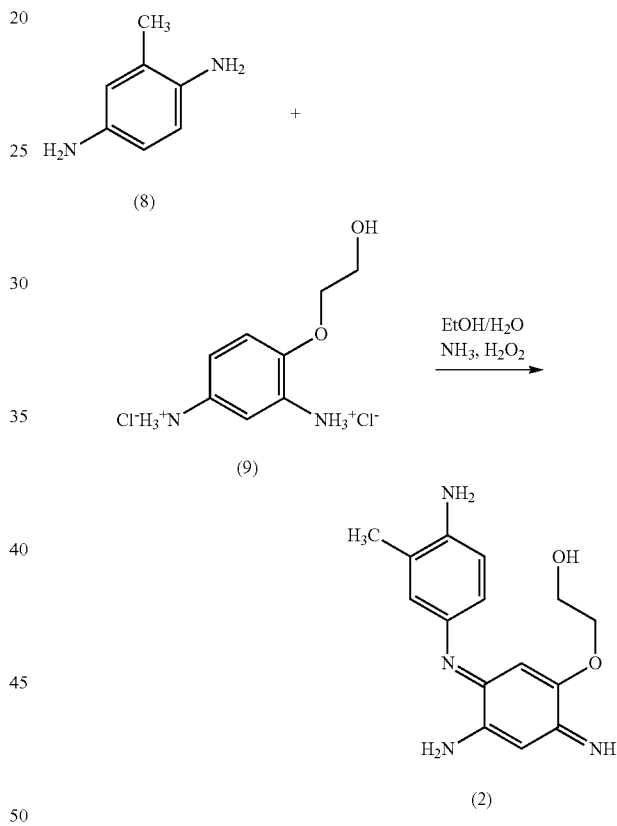

Under stirring, 0.61 g (0.005 mol) 2,5-diaminotoluene and 1.2 g (0.005 mol) 2,4-diaminophenoxyethanol dihydrochloride were dissolved in 15 mL ethanol. The clear solution was adjusted to pH 9.5 by the addition of an aqueous ammonium hydroxide (28%) solution. 17 mL of a hydrogen peroxide (6%) solution was added slowly dropwise within 30 minutes. The obtained product solution was stirred at 25° C. for 24 hours.

Then, 1.7 g manganese dioxide was added in portions to the above mixture. At the end of the gas formation, the manganese salt was removed by filtration. The obtained blue solution was evaporated in vacuum. The blue residue was suspended in 30 mL of 2-propanol and 10 mL of ethyl acetate and stirred for one hour at 25° C. The precipitate was filtered-off using a suction filter, washed with 10 mL ethyl acetate and dried at 30° C. in vacuum.

Yield: 1.0 g (70%), black solid.

$^1$H NMR (DMSO-$d_6$): δ=2.1 (m, br, CH$_3$), 3.7 and 4.0 (m; 2H, CH$_2$), 5.1-5.3, 5.8-6.1, 6.3, 7.0-7.8, 8.1 and 8.9 (m; br, OH, NH2, Aryl-H, Diene-H, C=N<u>H</u>).

MS (ESI): 287.5 (M+H)$^+$.

Example 2: 2-[5-amino-4-[2-amino-5-(2-hydroxy-ethoxy)-4-imino-cyclohexa-2,5-diene-1-ylidene]amino]pyrazol-1-yl]ethanol

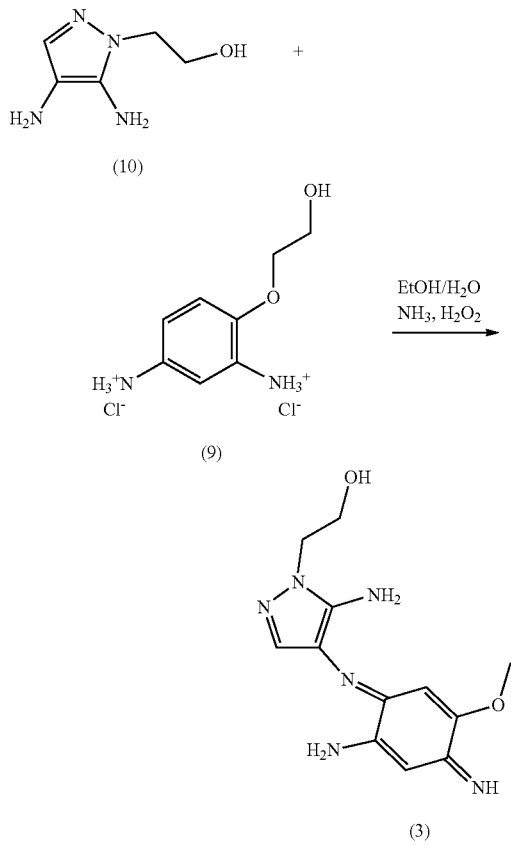

Under stirring, 1.2 g (0.005 mol) 4.5-diamino-1-(2-hydroxyethyl)pyrazole and 1.2 g 2.4-diaminophenoxyethanol dihydrochloride were dissolved in 20 mL ethanol. 20 mL of deionized water were added to get a clear red solution. Adjustment to pH 9.5 was done by the addition of around 1 mL of ammonium hydroxide (28%) solution. 17 mL of a hydrogen peroxide (6%) solution was added slowly dropwise within 30 minutes. This product solution was stirred at 25° C. for 24 hours. 1.7 g manganese dioxide was added portion wise. When the foaming and oxygen development had stopped, the manganese salt was removed by filtration. The obtained product solution was concentrated in vacuum. The red residue was suspended in 30 mL of 2-propanol and 10 mL of ethyl acetate and stirred for one hour at 25° C. The precipitate was filtered-off with a suction filter, washed with 10 mL ethyl acetate and dried at 30° C. in vacuum.

Yield: 1.2 g (78%), dark red solid.

$^1$H NMR (DMSO-$d_6$): δ=3.7-3.9 and 4.0-4.2 (m; each 2H, 2×CH$_2$), 4.90 (m; 2H, 2×OH), 5.9, 6.4 and 7.8 (s; 2H, Aryl and Diene-H), 7.3 (m, br, NH$_2$), 8.25 (m, br, NH).

Example 3: 4-[5-amino-1-(2-hydroxyethyl)pyrazol-4-yl]iminonaphthalen-1-one

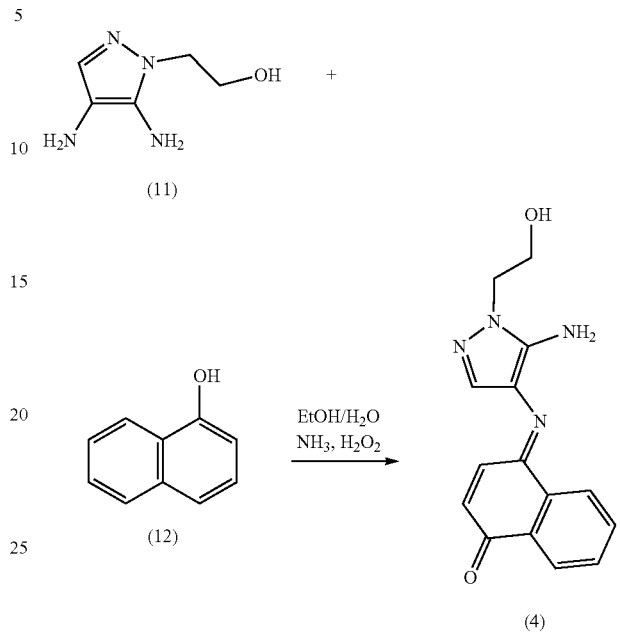

Under stirring, 1.2 g (0.005 mol) 4.5-diamino-1-(2-hydroxyethyl)pyrazole were dissolved in 40 mL of ethanol/water mixture (1:1 v/v). To this solution, a solution of 0.72 g (0.005 mol) 1-naphthol in 20 mL of an ethanol/water mixture (1:1 v/v) was added. The stirred solution was adjusted to pH 9.5 by the addition of around 1 mL of an aqueous ammonium hydroxide (28%) solution. 17 mL of a hydrogen peroxide (6%) solution were added slowly dropwise within 30 minutes. The solution kept stirring for another two hours. Then the red precipitate was filtered off. The solid residue was suspended in 200 mL of water and stirred for 15 minutes at 25° C. The solid was isolated by filtration using a suction filter, washed with 150 mL of water and dried at 50° C. in vacuum.

Yield: 1.1 g (78%), dark red solid.

$^1$H NMR (DMSO-$d_6$): δ=3.73 and 4.04 (m; each 2H, CHO), 4.94 (m; 1H, OH), 6.61 (m; 2H, NH$_2$), 7.55 and 7.70 (m; each 1H, Diene-H), 7.80 (s; 1H, Aryl-H), 8.0-8.1 (m, Aryl-H), 8.76 (m; Aryl-H).

MS (ESI): 283.3 (M+H)$^+$.

Example 4: 5-amino-4-(4-hydroxy-2-methyl-phenyl)imino-2-methyl-cyclohexa-2,5-diene-1-one

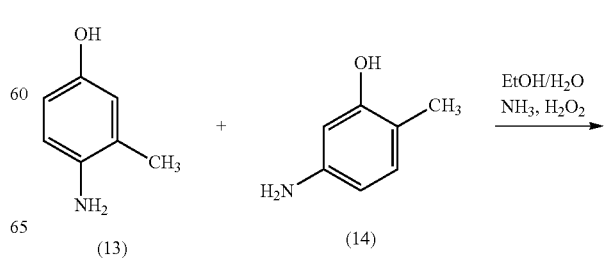

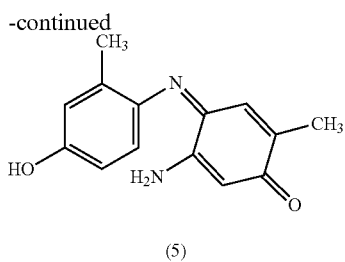

(5)

Under stirring, 0.61 g (0.005 mol) 3-methyl-4-aminophenol were dissolved in 40 mL of an ethanol/water mixture (1:1 v/v). To this solution, a solution of 0.61 g (0.005 mol) 4-amino-2-hydroxytoluene in 40 mL of an ethanol/water mixture (1:1 v/v) was added in one portion.

The stirred solution was adjusted to pH 9.5 by the addition of around 1 mL of an aqueous ammonium hydroxide (28%) solution. 17 mL of a hydrogen peroxide (6%) solution were added slowly dropwise within 30 minutes. The reaction mixture was stirred for 8 hours at 25° C. 1.4 g of manganese dioxide was added and stirring was continued until the foaming stopped. The solid residue was removed by filtration. The mother liquor was evaporated to dryness. The crude product was suspended in a mixture of 2-propanol and ethyl acetate and stirred for one hour at 25° C. The precipitate was filtered-off with a suction filter, washed with 10 mL ethyl acetate and dried at 30° C. in vacuum.

Yield: 0.8 g (66%), red solid.
MS (ESI): 243.2 $(M+H)^+$.

Example 5: 2-amino-6-(4-hydroxy-2-methyl-phenyl)imino-pyridine-3-one

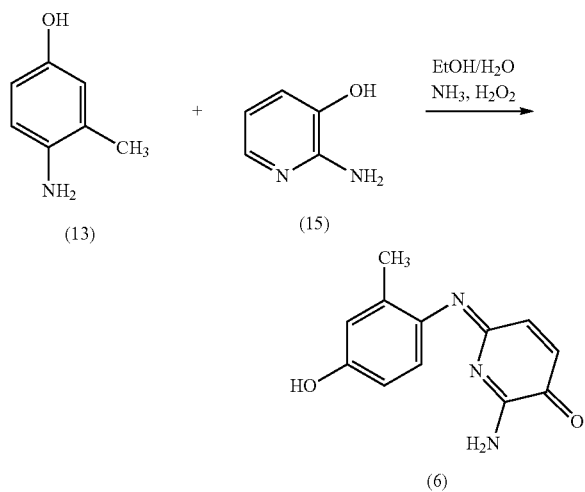

0.61 g (0.005 mol) 3-methyl-4-aminophenol and 0.55 g (0.005 mol) 2-amino-3-hydroxypyridine were reacted and worked-up as described in example 4.
Yield: 0.8 g (70%), red solid.
MS (ESI): 230.1 $(M+H)^+$.

B. Application Examples

To determine the wash fastness two sets of hair tresses were dyed under the same conditions. One set the dyed tresses was washed with a commercial shampoo (Goldwell definition Color & Highlights, color-conditioner shampoo) using approx. 0.5 g shampoo for each tress under tap water (water temperature: 37° C.+/−1° C.; flow rate 5-6 l/min). Finally, the tresses were rinsed under tap water, pressed out with a paper towel, combed and dried with a hair dryer or at room temperature. This procedure was repeated 10 times.

Example B1

0.5% of the dye of Example 1 was dissolved in a 5% solution of a non-ionic surfactant (Plantacare® 200UP, Henkel) adjusted to pH 9.5 using citric acid and monoethanolamine. This blue dyeing solution was applied on the dry hair (two blond and two damaged hair strands) and allowed to stand for 20 minutes at room temperature. Then, the strands were rinsed under tap water and dried 12 hours.

Example B2

0.5% of the dye of Example 1 was dissolved in a 5% solution of a non-ionic surfactant (Plantacare 200UP, Henkel) adjusted to pH 5.0 using citric acid and monoethanolamine. This blue dyeing solution was applied on the dry hair (two blond and two damaged hair strands) and allowed to stand for 20 min. at room temperature. Then, the strands were rinsed under tap water and dried 12 hours.

Example B3

0.25% of the dye of Example 1 was dissolved in a 5% solution of a non-ionic surfactant (Plantacare 200UP, Henkel) adjusted to pH 9.5 using citric acid and monoethanolamine. This blue dyeing solution was applied on the dry hair (two blond and two damaged hair strands) and allowed to stand for 20 min. at room temperature. Then, the strands were rinsed under tap water and dried 12 hours.

Example B4

0.25% of the dye of Example 1 was dissolved in a 5% solution of a non-ionic surfactant (Plantacare 200UP, Henkel) adjusted to pH 5.0 using citric acid and monoethanolamine. This blue dyeing solution was applied on the dry hair (two blond and two damaged hair strands) and allowed to stand for 20 min. at room temperature. Then, the strands were rinsed under tap water and dried 12 hours.

Example B5

Solution A: 0.5% of the dye of Example 1 was dissolved in a 5% solution of a non-ionic surfactant (Plantacare 200UP, Henkel) adjusted to pH 9.5 using citric acid and monoethanolamine.

Solution B: 0.1% of Basic Red 51 was dissolved in a 5% solution of a non-ionic surfactant (Plantacare 200UP, Henkel) adjusted to pH 9.5 using citric acid and monoethanolamine. 4 g of solution A and 4 g of solution B were mixed and applied on the dry hair (two blond and two damaged hair strands) and allowed to stand for 20 min. at room temperature. Then, the strands were rinsed under tap water and dried 12 hours.

Example B6

0.5% solution of the dye of example 1 adjusted to pH 10 with ammonia was mixed with the same weight of 6% hydrogen peroxide solution.

This mixture at pH 10 (0.25% of the dye) was applied with a brush on two hair strands (two blond and two damaged hair strands). After 30 min. at room temperature the tresses were rinsed, shampooed, rinsed and dried.

Example B7

1% solution of the dye of example 1 adjusted to pH 10 with ammonia was mixed with the same weight of 6% hydrogen peroxide solution.

This mixture at pH 10 (0.5% of the dye) was applied with a brush on two hair strands (two blond and two damaged hair strands). After 30 min. at room temperature the tresses were rinsed, shampooed, rinsed and dried.

Example B8

0.5% of the dye of Example 2 was dissolved (not complete) in a 5% solution of a non-ionic surfactant (Plantacare 200UP, Henkel) adjusted to pH 9.5 using citric acid and monoethanolamine.

This red dyeing solution was applied on the dry hair (two blond and two damaged hair strands) and allowed to stand for 20 min. at room temperature. Then, the strands were rinsed under tap water and dried 12 hours.

Example B9

0.5% of the dye of Example 2 was dissolved (not complete) in a 5% solution of a non-ionic surfactant (Plantacare 200UP, Henkel) adjusted to pH 9.5 using citric acid and monoethanolamine and mixed with Ethanol 1:1 to dissolve more of the dye.

This red dyeing solution was applied on the dry hair (two blond and two damaged hair strands) and allowed to stand for 20 min. at room temperature. Then, the strands were rinsed under tap water and dried 12 hours.

Example B10

1% solution of the dye of Example 2 adjusted to pH 10 with ammonia was mixed with the same weight of 6% hydrogen peroxide solution.

This mixture at pH 10 (0.5% of the dye) was applied with a brush on two hair strands (two blond and two damaged hair strands). After 30 min. at room temperature the tresses were rinsed, shampooed, rinsed and dried.

Example B11

0.5% of the dye of Example 3 was dissolved (not complete) in a 5% solution of a non-ionic surfactant (Plantacare 200UP, Henkel) adjusted to pH 9.5 using citric acid and monoethanolamine. This red dyeing solution was applied on the dry hair (two blond and two damaged hair strands) and allowed to stand for 20 min. at room temperature. Then, the strands were rinsed under tap water and dried 12 hours.

Example B12

0.5% of the dye of Example 3 was dissolved (not complete) in a 5% solution of a non-ionic surfactant (Plantacare 200UP, Henkel) adjusted to pH 9.5 using citric acid and monoethanolamine and mixed with Ethanol 1:1 to dissolve more of the dye.

This red dyeing solution was applied on the dry hair (two blond and two damaged hair strands) and allowed to stand for 20 min. at room temperature. Then, the strands were rinsed under tap water and dried 12 hours.

Example B13

1% solution of the dye of Example 3 adjusted to pH 10 with ammonia was mixed with the same weight of 6% hydrogen peroxide solution.

This mixture at pH 10 (0.5% of the dye) was applied with a brush on two hair strands (two blond and two damaged hair strands). After 30 min. at room temperature the tresses were rinsed, shampooed, rinsed and dried.

| Dye | substance color | hair type | color | intensity | brilliance | dE color uptake | dE* washing fastness 10x washed with shampoo | Application Example |
|---|---|---|---|---|---|---|---|---|
| Ex 1 | Black solid | blond | blue | good | good | 62.8 | 10.6 | B1 |
| Ex 1 | Black solid | bleached | blue | good | good | 49.8 | 9.2 | B1 |
| Ex. 1 | Black solid | blond | blue | good | good | 54.3 | 12.8 | B2 |
| Ex. 1 | Black solid | bleached | blue | good | good | 49.6 | 5.4 | B2 |
| Ex. 1 | Black solid | blond | blue | good | good | 52.3 | 8.5 | B3 |
| Ex. 1 | Black solid | bleached | blue | good | good | 48.0 | 10.3 | B3 |
| Ex. 1 | Black solid | blond | blue | good | good | 52.5 | 15.5 | B4 |
| Ex. 1 | Black solid | bleached | blue | good | good | 48.0 | 11.3 | B4 |
| Ex. 1 and Basic Red 51 | | blond | violet | good | good | 63.6 | 7.4 | B5 |
| Ex. 1 and Basic Red 51 | | bleached | violet | good | good | 50.4 | 15.6 | B5 |
| Ex. 1 | Black solid | blond | blue | good | good | 49.4 | 5.7 | B6 |
| Ex. 1 | Black solid | bleached | blue | good | good | 37.8 | 11.8 | B6 |
| Ex. 1 | Black solid | blond | blue | good | good | 55.5 | 4.5 | B7 |
| Ex. 1 | Black solid | bleached | blue | good | good | 41.1 | 7.3 | B7 |
| Ex. 2 | Dark red solid | blond | red | weak | weak | 20.0 | 7.3 | B8 |
| Ex. 2 | Dark red solid | bleached | red | middle | good | 38.4 | 11.0 | B8 |
| Ex. 2 | Dark red solid | blond | red | weak | weak | 22.8 | 2.9 | B9 |
| Ex. 2 | Dark red solid | bleached | red | middle | good | 41.0 | 9.5 | B9 |
| Example 2 | Dark red solid | blond | red | good | good | 60.2 | 3.9 | B10 |
| Example 2 | Dark red solid | Middle blond | red | good | good | 26.7 | 2.7 | B10 |
| Example 2 | Dark red solid | bleached | red | good | good | 54.5 | 7.1 | B10 |
| Example 3 | Dark red solid | blond | red | good | good | 54.5 | 9.7 | B11 |
| Example 3 | Dark red solid | bleached | red | good | good | 53.2 | 7.3 | B11 |
| Example 3 | Dark red solid | blond | red | good | good | 43.5 | 4.0 | B12 |

-continued

| Dye | substance color | hair type | color | intensity | brilliance | dE color uptake | dE* washing fastness 10x washed with shampoo | Application Example |
|---|---|---|---|---|---|---|---|---|
| Example 3 | Dark red solid | bleached | red | good | good | 53.0 | 8.5 | B12 |
| Example 3 | Dark red solid | blond | red | weak-middle | weak | 28.8 | 0.8 | B13 |
| Example 3 | Dark red solid | Middle blond | red | weak | weak | 10.5 | 1.3 | B13 |
| Example 3 | Dark red solid | bleached | red | good | good | 44.4 | 11.9 | B13 |

The invention claimed is:

1. A composition for dyeing keratin fibers comprising
a. at least one azomethine compound selected from

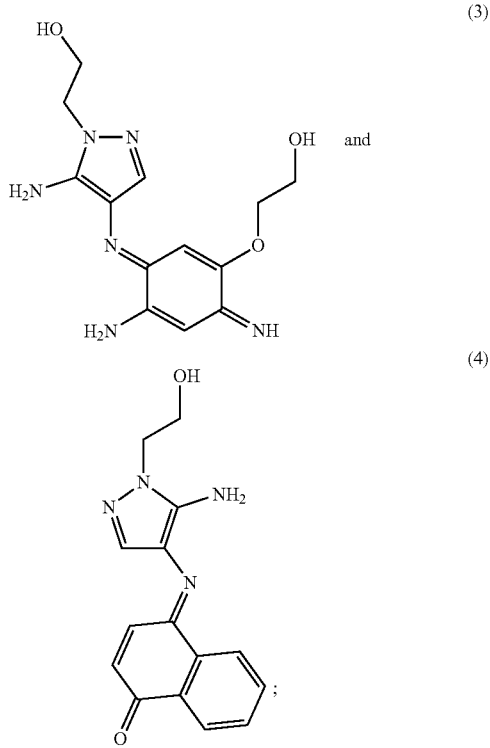

and
b. water.

2. The composition according to claim 1, wherein an amount of azomethine compound is in the range from 0.001% to 10% by weight based on the total weight of composition.

3. The composition according to claim 1 having a pH in the range from 3 to 12.

4. The composition according to claim 1 further comprising a non-ionic surfactant.

5. The composition according to claim 1 further comprising an organic solvent selected from the group consisting of $C_1$-$C_4$ alkanols, polyols, polyol ethers, and aromatic alcohols.

6. The composition according to claim 1 further comprising at least one oxidation dye in an amount in the range of 0.001% to 10% by weight based on the total weight of composition, and at least one coupler in an amount in the range of 0.001% to 10% by weight based on the total weight of composition.

7. The composition according to claim 1 further comprising an adjuvant in amount in the range of 0.01% to 20% by weight based on the total weight of composition, wherein the adjuvant is at least one selected from the group consisting of surfactants, polymers, thickeners, antioxidants, penetrants, solubilizers, sequestrants, fragrances, buffers, dispersants, conditioning agents, film-forming agents, ceramides, preserving agents, opacifiers, conductive polymers, and mixtures thereof.

8. A process for dyeing keratin fibers, comprising applying a composition according to claim 1 to the-wet or dry fibers for a time that is sufficient to obtain the desired coloration, after which the fibers are rinsed, optionally washed with shampoo and rinsed again, and the resulting fibers are dried or left to dry to obtain dyed keratin fibers.

9. The process according to claim 8 for dyeing human hair.

10. A process for lightening keratin fibers, comprising applying
(i) a dye composition according to claim 1, free of oxidizing agent, and
(ii) a cosmetic composition comprising one or more oxidizing agents to the fibers; compositions (i) and (ii) being applied to the keratin fibers sequentially or simultaneously for a time that is sufficient to obtain the desired lightening, and the fibers are then rinsed, optionally washed with shampoo and rinsed again, and the resulting fibers are dried or left to dry.

* * * * *